United States Patent [19]
Girotti et al.

[11] Patent Number: 6,034,291
[45] Date of Patent: Mar. 7, 2000

[54] CATALYTIC COMPOSITION AND PROCESS FOR THE ALKYLATION AND/OR TRANSALKYLATION OF AROMATIC COMPOUNDS

[75] Inventors: Gianni Girotti, Novara; Oscar Cappellazzo, Alghero; Elena Bencini, Virgilio; Giannino Pazzuconi, Pavia; Carlo Perego, Carnate, all of Italy

[73] Assignee: Enichem S.p.A., Milan, Italy

[21] Appl. No.: 08/988,379

[22] Filed: Dec. 10, 1997

[30] Foreign Application Priority Data

Dec. 12, 1996 [IT] Italy ................................. MI96A2603

[51] Int. Cl.⁷ ........................................ C07C 2/54
[52] U.S. Cl. .................. 585/323; 585/467; 585/475; 502/63; 502/64
[58] Field of Search ..................... 585/467, 475, 585/323; 502/63, 64

[56] References Cited

U.S. PATENT DOCUMENTS

| | | | |
|---|---|---|---|
| 4,968,405 | 11/1990 | Wachter . | |
| 5,118,896 | 6/1992 | Steigelmann et al. . | |
| 5,182,242 | 1/1993 | Marler | 502/66 |
| 5,672,799 | 9/1997 | Perego et al. . | |
| 5,811,612 | 9/1998 | Girotti et al. | 585/467 |

FOREIGN PATENT DOCUMENTS

| | | |
|---|---|---|
| 0550 270 | 7/1993 | European Pat. Off. . |
| 0687 500 | 12/1995 | European Pat. Off. . |
| WO 96/14269 | 5/1996 | WIPO . |

*Primary Examiner*—Thomas Dunn
*Attorney, Agent, or Firm*—Oblon, Spivak, McClelland, Maier & Neustadt, P.C.

[57] ABSTRACT

A catalytic composition is described for the alkylation and/or transalkylation of aromatic hydrocarbons consisting of beta zeolite, as such or modified by the isomorphous substitution of aluminum with boron, iron or gallium or by the introduction of alkaline and/or earth alkaline metals following an ion-exchange process, and an inorganic ligand, wherein the extrazeolite porosity, i.e. the porosity obtained by adding the mesoporosity and macroporosity fractions present in the catalytic composition itself, is such that a fraction of at least 25% is composed of pores with a radius higher than 100 Å, said composition being characterized by a total volume of extrazeolitic pores greater than or equal to 0.80 ml/g.

30 Claims, 8 Drawing Sheets

CATALYTIC COMPOSITION AND PROCESS FOR THE ALKYLATION AND/OR TRANSALKYLATION OF AROMATIC COMPOUNDS

BACKGROUND OF THE INVENTION

FIELD OF THE INVENTION

The present invention relates to catalytic compositions consisting of beta zeolite (as such or modified) and a ligand, characterized by particular porosity characteristics, which can be used in processes for the alkylation of aromatic hydrocarbons with light olefins, in particular benzenes with $C_2$–$C_4$ olefins and more specifically benzene with ethylene to give ethylbenzene and benzene with propylene to give cumene. The catalytic composition of the present invention can also be used in the transalkylation of aromatic hydrocarbons with polyalkylated aromatic hydrocarbons, especially benzene with diethylbenzene, and possibly triethylbenzene, to give ethylbenzene and benzene with diisopropylbenzene, and possibly triisopropylbenzene, to give cumene.

DESCRIPTION OF THE BACKGROUND

Former processes, still widely used in the petro-chemical industry for the production of alkylaromatics, and in particular cumene and ethylbenzene, comprise the use of a catalyst based on phosphoric acid and infusorial earth in a fixed bed for cumene and $AlCl_3$ in slurry for ethylbenzene and cumene.

These processes however create problems relating to environment and safety; in fact the use of these catalysts is particularly problematical due to corrosion, the by-production of toxic organic products and the disposal of the exhausted catalysts.

The possibility of substituting these catalysts with non-polluting, non-corrosive and regenerable materials such as for example zeolite catalysts, has been known for some time.

The use of X and Y zeolites for the preparation of cumene was disclosed for the first time in 1965 (Minachev, Kr. M., Isakov, Ya.I., Garanin, V. I., Piguzova, L. I., Bogomov, V. I., and Vitukina, A. S., Neftekhimiya 5 (1965) 676). Subsequently Venuto et al. (Venuto, P. B., Hamilton, L. A., Landis, P. S., and Wise, J. J., J. Catal.5, (1966) 81) described the alkylation of benzene with light olefins, such as propylene and ethylene, catalyzed by zeolites with a faujasitic structure (X and Y), consequently with wide pores. These zeolites can be stabilized by exchange with rare earth. U.S. Pat. No. 3,251,897 describes the alkylation of aromatics in liquid phase, catalyzed by porous crystalline alumino-silicates, among which X, Y and mordenite. U.S. Pat. No. 4,292,458 describes the use of zeolites of the type ZSM-5, in particular a boralite with a ZSM-5 type structure, capable of catalyzing the alkylation of benzene with propylene. This type of zeolitic system however, perhaps owing to channels which are too small, only allows the production of cumene with rather low selectivities.

It can therefore generally be said that zeolites are active in the alkylation of aromatics with olefins, but have different kinds of behaviour with respect to the selectivity. The alkylation reaction is in fact accompanied by subsequent secondary reactions such as polyalkylation, and parallel reactions such as the oligomerization of olefins. The oligomers can then in turn alkylate the aromatic giving heavy alkylated products or crack to light olefins, different from the main reagent, producing by subsequent alkylation other alkylated by-products.

In order to increase the selectivity to monoalkylated products, it is customary in organic chemistry to operate in the presence of an excess of aromatic hydrocarbon, i.e. with high aromatic/olefin ratios (Groggins, P. H., "Unit Processing in Organic Synthesis", 5th ed., McGraw Hill, 1958). In addition, owing to the exothermicity of the reaction, to operate in the presence of an excess of aromatic or an inert solvent allows a better control of the temperature. Alternatively, in order to maintain the temperature within a preferred range and reduce the by-production of aromatic polyalkylated products, the catalyst can be distributed on the reactors in various layers and a quench carried out between one layer and another with inert solvents and/or part of the aromatic and/or part of the olefin. In this way high aromatic/olefin ratios can be obtained on the single layer, without increasing the overall ratio itself, with an obvious advantage for the subsequent separation and recycling of the aromatic. This way of operating, which was already common practice in processes for production based on supported phosphoric acid, is also used at present in production processes of ethylbenzene in vapor phase catalyzed by ZSM-5 (SRI Report Nr. 22A, September 1972, Menlo Park, Calif.).

Other methods for increasing the selectivity to monoalkylated products are those which exploit the capacity of acid zeolites active in alkylation, of transalkylating. This characteristic has been known for some time and was described for the first time in 1966 in Venuto, P. B., Hamilton, L. a., Landis, P. S., and Wise, J. J., J. Catal.5, (1966)81. Unlike zeolites supported phosphoric acid is not capable of catalyzing the transalkylation reaction of polyalkylbenzenes and in particular polyisopropylbenzenes (SRI Report Nr. 22A, September 1972, Menlo Park, Calif.).

As in alkylation, also in transalkylation, the catalytic performances of zeolites vary not only in terms of activity but mainly selectivity. The alkylation reaction is more critical however than transalkylation: the former is very exothermic whereas transalkylation is practically athermic and does not therefore have problems of temperature control. In addition, the absence of olefins during the transalkylation excludes the formation of by-products deriving therefrom and reduces problems of pitching and deactivation caused by these. Consequently, whereas it is possible to assume that a zeolite which is active and selective in alkylation is likewise also in transalkylation, under suitable operating conditions, a zeolite which is active in transalkylation will definitely also be as such in alkylation, but its behaviour with respect to selectivity cannot be predicted. Similarly a zeolite which is stable in alkylation will be likewise also in transalkylation, but the opposite may not necessarily be true. Patents which describe the use of zeolites with small, medium and large pores for the transalkylation reaction of polyalkylaromatics, in gas, liquid or mixed phase are for example U.S. Pat. Nos. 3,385,906, 4,169,111 and EP 308097. The transalkylation reaction of polyalkylaromatics with aromatic hydrocarbons, in particular with benzene, to give monoalkylaromatics is a reaction which is limited by the equilibrium which under suitable conditions and with appropriate catalysts takes place already in the alkylation phase. In particular, U.S. Pat. Nos. 3,772, 398 and 3,776,971 disclose that the transalkylation reaction already takes place during the alkylation of benzene with propylene catalyzed by a Y zeolite exchanged with rare earth. The conversion profiles, obtained by varying the residence times in the alkylator show that diisopropylbenzenes reach a maximum and then diminish, even before the propylene has been completely used up. The selectivity of cumene can therefore be increased by increasing the residence times in the alkylator and consequently approaching the equilibrium values. In line with what is specified above, even better results can be obtained by recycling the polyalkylated by-products in the alkylation reactor where the catalyst favours transalkylation increasing the overall yield to monoalkylated product. This industrial practice used for both the catalyst $AlCl_3$, and for the Mobil-Badger process in the case of the production of ethylbenzene, is also described in Keading, W. W., and Holland, R. E., J. Catal. 109(1988) 212, which, in order to increase the yields to cumene, suggests recycling the diisopropylbenzenes deriving from the alkylation of benzene with propylene, catalyzed by ZSM-5, to the alkylation reactor.

The transalkylation reaction of polyaromatics can also be appropriately carried out separately from the alkylation step, operating on the polyalkylated products recovered downstream of the alkylation. For example, the use of zeolitic catalysts to transalkylate polyalkylated products in one transalkylation step separate from the alkylation is described in U.S. Pat. Nos. 3,385,906, 4,774,377, 4,168,111 and EP 308097.

At present the best results in terms of activity in the alkylation of aromatics with $C_2$–$C_4$ olefins, in liquid phase, are obtained by using beta zeolite as alkylation catalyst. EP 432,814 described the use of this zeolite for the first time and better results are shown with respect to the zeolites of the prior art ZSM-5, Y and ZSM-12. Subsequently the akylation and transalkylation of aromatics catalyzed by beta zeolite was also described-in EP 439632. For use in industrial catalyst fixed-bed reactors, it is necessary for the zeolitic catalysts to be in the form of pellets or other suitable forms, and for them to have excellent mechanical characteristics in terms of crushing strength and loss on attrition. Good mechanical characteristics in fact enable a minimum or zero production of fines during the charging of the catalyst into the industrial reactor and, above all, allow the reactor to run with high flow-rates of the reagents, i.e. with high space velocities (WHSV), thus increasing the hourly productivity which can be obtained with the same reactor volume available. The necessity for high mechanical characteristics is much greater in the case of regenerable catalysts which must frequently undergo thermal regeneration treatment, which causes strong structural stress. In case of thermal regenerations carried out "off-site", the use of a catalyst with insufficient mechanical characteristics would lead to considerable losses in material during the numerous charging and discharging of the exhausted and regenerated catalyst. This aspect is therefore of primary importance if the regenerable catalyst is used in existing industrial plants, where it may not be possible to carry out the thermal regeneration in situ. The achievement of excellent mechanical characteristics is however generally hindered by the necessity of maintaining certain porosity characteristics which are necessary for the reaction in which the catalyst is used.

EP 687500 describes catalysts prepared starting from beta zeolite and an inorganic ligand, used in alkylation and transalkylation reactions of aromatics with light olefins, which have specific porosity characteristics which guarantee high performances in terms of duration and therefore productivity for each reaction cycle, together with excellent mechanical characteristics such as crushing strength and resistance to abrasion. The catalytic composition of the present invention, for the alkylation and/or transalkylation of aromatic compounds consists of:

beta zeolite, as such or modified by the isomorphous substitution of aluminum with boron, iron or gallium or modified by the introduction of alkali and/or alkaline earth metals by means of ion exchange processes;

an inorganic binder, preferably selected from oxides of silicon, aluminum, zirconium, magnesium or natural clays or combinations of these, and is characterized in that the extrazeolite porosity, i.e. the porosity obtained by summing the mesoporosity and macroporosity fractions present in the catalytic composition itself (consequently excluding the contribution of microporosity relating to the beta zeolite), is such that a fraction of at least 25%, preferably at least 35%, is composed of pores with a radius higher than 100 Å. The productivity, and consequently the duration, for each reaction cycle is in fact more than double if the catalyst has that particular porosity which is the main characteristic of the invention. The role of the porous structure claimed is to reduce the deactivation rate of the catalyst i.e. the deposit velocity of the carbonaceous products responsible for the deactivation which is formed during the reaction.

We have now found that in the case of catalysts prepared according to EP 687500 starting from beta zeolite and an inorganic binder, used in alkylation reactions of aromatics with light olefins or in transalkylation reactions, there is a surprising effect of the total EPV (Extrazeolite Pore Volume) porosity value.

The catalysts claimed have particular porosity characteristics which guarantee even higher performances in terms of duration and therefore productivity for each reaction cycle, maintaining good mechanical characteristics, such as crushing strength and resistance to abrasion.

The present invention therefore relates to a catalytic composition for the alkylation and/or transalkylation of aromatic hydrocarbons, consisting of:

beta zeolite, as such or modified by means of the isomorphous substitution of aluminum with boron, iron or gallium or modified by the introduction of alkali and/or alkaline earth metals following ion-exchange processes;

an inorganic binder, which has an extrazeolite porosity, i.e. a porosity obtained by adding the mesoporosity and macroporosity fractions present in the catalytic composition itself, which is such that a fraction of at least 25% is composed of pores with a radius higher than 100 Å, and is characterized by a total volume of extrazeolitic pores greater than or equal to 0.80 ml/g.

Figure 1:
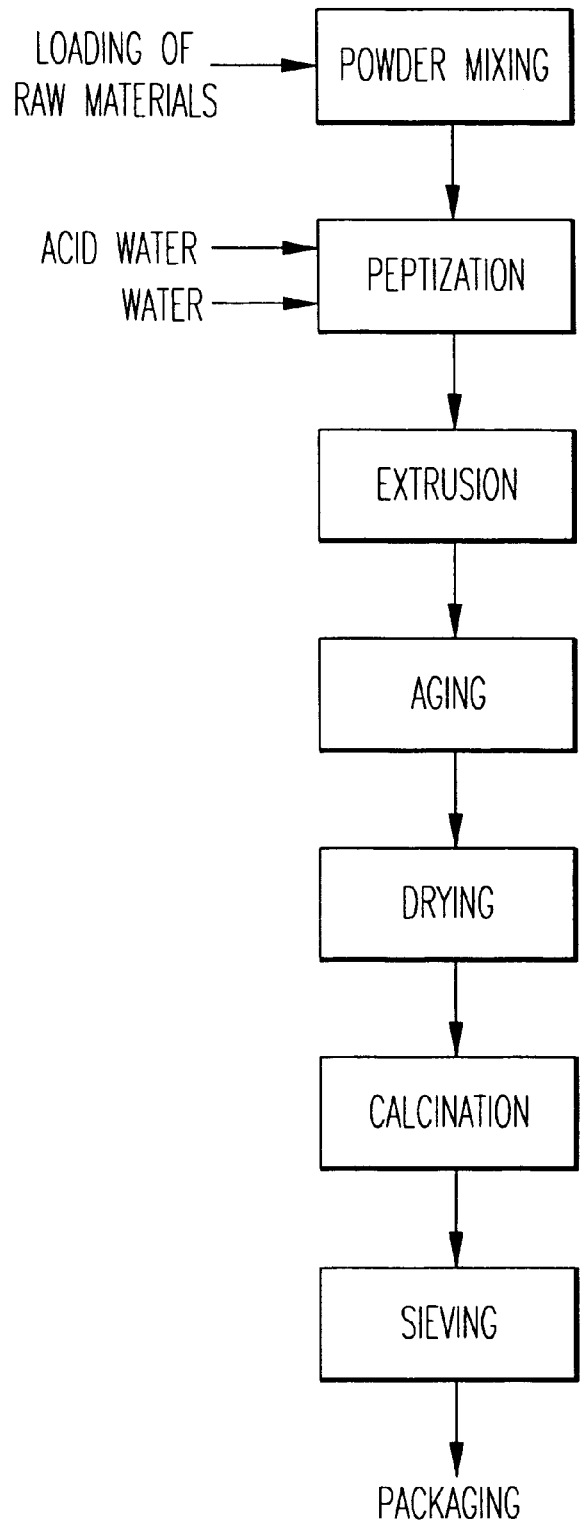
FIG. 1 shows a process embodiment for producing the catalyst of the invention.

Extrazeolite porosity refers to the porosity obtained by adding the mesoporosity and macroporosity fractions present in the catalytic composition itself and therefore excludes the contribution of microporosity relating to the Beta zeolite. The terms microporosity, mesoporosity and macroporosity are used herein in accordance with the Dubinin classification specified in Surface Area Determination-IUPAC-Proceedings in the International Symposium on Surface Area Determination, Bristol U.K. 1969, and correspond to the following ranges of porosity:

pore radius Å>1000 macroporosity

1000> pore radius Å>15 mesoporosity

15> pore radius Å microporosity

The inorganic ligand is preferably selected from the oxides of silicon, aluminum, magnesium or natural clays or combinations of these.

According to a preferred aspect the extrazeolite porosity is such that a fraction of at least 35% is composed of pores with a radius higher than 100 Å.

The porosity in the fraction with a radius which is greater than 450 Å should preferably be less than 0.25 cc/g when the diameter of the catalytic particles is less than or equal to 0.8 mm.

Beta zeolite, made known in U.S. Pat. No. 3,308,069, is a synthetic, porous, crystalline material having the composition

$$[(x/n)M(1\pm0.1-x)TEA]AlO_2 \cdot ySiO_2 \cdot wH_2O$$

wherein x is less than 1, y is between 5 and 100, w is between 0 and 4, M is a metal of groups IA, IIA, IIIA or a transition metal and TEA is tetraethylammonium.

Beta zeolites which are particularly useful for the present invention are represented by the formula:

$$[(x/n)M(1\pm0.1-x)Z]AlO_2 \cdot ySiO_2 \cdot wH_2O$$

wherein x is less than 1, preferably less than 0.75, y is between 5 and 100, w between 0 and 4, M is a metal of groups IA, IIA, IIIA or a transition metal, n is the valence of M, Z is a hydrogen, ammonium ion or an organic cation.

According to a preferred aspect, the beta zeolite of the catalytic composition of the present invention is in acid form, i.e. in the form in which most of the cationic sites are occupied by hydrogen ions.

Modifications of beta zeolite, which can also be used for our invention, can be obtained by the partial or total isomorphous substitution of aluminum with boron: patent BE-877205 for example describes a porous crystalline boron-silicate called boralite-B; EP-55046 patent application discloses a zeolite isomorphous with beta zeolite in which the aluminum has been partially substituted with boron, iron or gallium.

Another modification of beta zeolite which can be used for the present invention is that described in EP 629599, i.e. a beta zeolite containing controlled quantities of alkyali, alkaline earth and/or nickel.

The catalyst of the present invention is prepared starting from beta zeolite and an inorganic binder by means of a particular process which is a further aspect of the present invention.

In forming processes of catalysts in pellet form, using binders such as alumina, there is a series of variables to be adopted well-known to experts in forming processes, for obtaining the desired mechanical characteristics and pore size distribution (PSD). Also with respect to the total EPV extrazeolite porosity there are, in principle, many ways of increasing its value during the forming process, such as for example by carrying out an incomplete peptization of the ligand, adopting ligands with a lower dispersibility (DI) coefficient, using weaker acids or lower concentrations of acid, adding to the mixture of zeolite and ligand, substances suitable for creating porosity in the calcination phase of the catalyst. Generally however, the results obtained by varying the parameters of the process are accompanied by a significant drop in the mechanical charactertistics if the increase in the total EPV extrazeolite porosity is significant. The addition of substances suitable for creating porosity in the subsequent calcination phase of the catalyst generally produces more evident results in terms of an increase in EPV, which is obtained however by increasing the porosity generally in the highest mesoporosity and macroporosity zone; this causes a drastic deterioration in the mechanical characteristics of the catalyst, mainly in the case of materials which have a percentage of binder for example of between 20 and 50% by weight as in the case of zeolitic catalysts.

We have found that by selecting for the preparation of the catalyst, a suitable form for the zeolitic component, it is possible to increase the EPV to the values claimed maintaining PSD values which are such that the extrazeolite porosity is composed of a fraction of at least 25% with pores having a radius higher than 100 Å, and the resulting catalyst has good mechanical characteristics.

The procedure for the preparation of the materials in accordance with the present invention comprises:

a) preparing a homogeneous mixture comprising beta zeolite whose cationic sites are ammonium and alkylammonium and an inorganic binder;

b) subjecting the mixture thus obtained to forming;

c) calcining the product resulting from step (b).

This preparation procedure, characterized by the use of a beta zeolite whose cationic sites are ammonium and alkylammonium form, is much simpler than that described in EP 687500 owing to the reduction in the number of unitary operations involved; it therefore allows a more efficient industrial production, with a reduction in out-of-specification or non-conformity products due to possible problems during the unitary operations which have been eliminated.

In step (a) the beta zeolite used has not undergone any calcination treatment and is therefore whose cationic sites are ammonium and alkylammonium ions, i.e. it is a beta zeolite in which the original metal cations from the synthesis have been exchanged with ammonium ions, and which still contains the alkylammonium ions used as templating agent for its synthesis. The exchange is carried out with the known techniques, for example by suspending the zeolite powder in an aqueous solution of an ammonium salt, which can be selected from acetate, nitrate; chloride, and by heating to a temperature of not more than 100° C. The operation can be repeated several times, alternating it with washings with demineralized water, to reach the desired exchange level.

The ligand is preferably selected from the oxides of aluminum, silicon, magnesium, natural clays or combinations of these.

In the mixture prepared in step (a), the beta zeolite in ammonia/alkylammonia form is mixed with the ligand in relative quantities ranging from 50:50 to 95:5, preferably between 70:30 and 90:10; this mixture can also contain peptizing agents (for example acetic acid) and plasticizers (e.g. methylcellulose).

The calcination in step (c) is carried out in air at a temperature ranging from 400 to 600° C. and can be preceded by an aging and drying step at a temperature ranging from room temperature to 200° C. In the case of catalytic compositions comprising beta zeolites containing controlled quantities of alkali, alkaline metals and/or nickel, after the calcination step there is a subsequent exchange to introduce calibrated quantities of an ion selected from $Na^+$, K$^+$, Ca$^{2+}$ or Ni$^{2+}$. The exchange is carried out with the known techniques, as described by R. P. Townsend, "Ion exchange in zeolites", Studies Surf. Scien. Cat., vol.58, pages 359–390, 1991. Sodium, potassium and calcium salts which can be used for the exchange are for example the corresponding acetates, nitrates and chlorides.

Any type of procedure can be used in step (b) for the forming of the catalyst of the present invention: the catalyst can in fact be prepared in tablets, bars, cylinders or any other form considered suitable for its use in alkylation reactions of aromatics with light olefins and in particular with ethylene and propylene. The extrusion procedure is preferably used, i.e. the forming of the catalyst in cylinders having small dimensions called pellets. This forming step, as described in EP 687500, is capable of inducing a porosity distribution which can be determined a priori and the parameters adopted during the forming of the catalyst are essential for controlling and obtaining an extrazeolite porosity having a fraction of at least 25% composed of pores with a radius higher than 100 Å. These parameters mainly relate to the extrusion back-pressure and the particle size of the beta zeolite and inorganic binder used. With the same components, the control of the extrusion back-pressure can be carried out by modifying several variables typical of an extrusion procedure, among which the type of machine used, the rotation rate of the compressing section, the diameter of the outlet holes or nozzles of the fresh extruded product, the humidity of the feeding into the extruder, the quantity and quality of peptizing agent possibly used for the preparation of the feeding into the extruder and the possible presence of particular substances suitable for giving plasticity and flowability during the extrusion. In the forming step it is therefore possible to determine the distribution of the porous structure of the catalyst by means of the above variables and experts in forming procedures for catalysts and in particular extrusion will certainly know the effect, contribution and role of the above variables in determining the distribution of the porosity in the structure of the catalyst and can therefore easily repeat the preparation process described above.

The catalytic material of the present invention proves to have a higher interconnection degree of the extrazeolitic porous network than materials which are not in accordance with the present invention. The measure of the interconnection degree existing between the pores, which is an important parameter for the distribution of the reagents through the catalyst pellets, is by necessity an indirect measurement. It can be carried out by elaborating the data of the absorption isotherm with nitrogen at the temperature of liquid nitrogen in the relative pressure zone corresponding to the mesoporosity. In this zone the presence of mesopores is in fact marked only by a type IV isotherm characterized by the presence of a hysteresis i.e. in a zone in which the absorption branch cannot be superimposed by the desorption branch.

An accentuation of the hysteresis of the experimental absorption isotherm of the nitrogen at the temperature of liquid nitrogen indicates a decrease in the connectivity degree of the extrazeolitic porous network of the catalyst subjected to analysis; this result should therefore be avoided or it would be even better to try and obtain an attenuation in the hysteresis, as this indicates a catalyst having good connectivity and therefore distribution inside the EPV.

In particular a form of hysteresis loop type A according to the De Boer classification, qualitatively indicates a mesoporosity essentially consisting of regular or cylindrical pores "open at both ends" (Introduction to Power Surface Area, chpt.9, Lowell, Seymour—Wiley Interscience publ. 1979) for which the evaporation of the liquid nitrogen contained therein during the desorption is not substantially influenced by the surrounding pores and therefore mainly depends on the pressure of the surrounding vapour phase (The Surface Area in Intermediate Pores, J.P.C. Broekhoff and J. H. de Boer in International Symposium on Surface Area Determination-Bristol, U.K., 1969—IUPAC).

A form of hysteresis loop type E indicates on the other hand pores of the "bottle-neck" type and generally relates to pores whose liquid contained therein is not directly in contact with the vapour phase during the desorption process; this is therefore a qualitative index of a lesser connectivity of the mesoporous network of the material under examination compared to a material characterized by a hysteresis loop type A.

A Sorptomatic 1900 Carlo Erba instrument was adopted for measuring the porosity using the physical adsorption technique of nitrogen at the temperature of liquid nitrogen, basically using the indications contained in chapters 12 and 13 and chapter 20 of the volume "Introduction to Powder Surface Area"—Lowell, Seymour—Wiley Interscience publ., 1979, with respect to the analysis conditions.

The catalytic composition of the present invention is particularly suitable in alkylation processes of aromatic hydrocarbons with light $C_2$–$C_4$ olefins, and particularly benzene with ethylene to give ethylbenzene and benzene with propylene to give cumene.

The alkylation reaction can be industrially carried out in continuous, semi-continuous or batch, and in gaseous phase, liquid phase or mixed phase; in order to maintain the temperature within a preferred range and reduce the by-production of aromatic polyalkylated products, the catalyst can be arranged in various layers in the reactor. A quench is carried out between one layer and another with inert solvents and/or part of the aromatic and/or part of the olefin.

Under appropriate conditions it is possible to obtain higher aromatic/olefin ratios on the single layer, without increasing the overall ratio itself, with an obvious advantage for the subsequent separation and recycling of the aromatic. The temperature control can be carried out not only by quenching the reagents and/or inert products, but also by inter-refrigeration between the layers, for example by the intersertion of refrigerants. The alkylation reaction can be appropriately carried out in two or more reactors in series, inter-refrigerated to control the temperature. The feeding of the olefins and/or aromatic can be suitably partialized among the various reactors and reactor layers, i.e. the olefin and/or the aromatic are added in more than one step; the olefin can optionally be diluted with the aromatic or with an inert product to favour the temperature control. The feeding of the olefin is in such a quantity as to obtain a molar ratio [Aromatic]/[Olefin] preferably between 1 and 20, more preferably between 2 and 8. The reaction temperature is between 100° C. and 300° C., preferably between 120° C. and 230° C., the pressure is between 10 atms and 50 atms, preferably between 20 atms and 45 atms; the WHSV space velocity is between 0.1 and 200 h$^{-1}$, preferably between 1 and 10 h$^{-1}$. It should be noted however that the combination between the temperature and pressure conditions actually adopted is preferably such as to guarantee that the alkylation reaction takes place at least partly in liquid phase, and that it more preferably takes place substantially in liquid phase.

Using the catalytic composition of the present invention in alkylation processes a higher duration and productivity of the catalyst itself can be obtained for each single reaction cycle with respect to the materials of the prior art.

The catalytic composition of the present invention is also particularly useful in the transalkylation of aromatic hydrocarbons with polyalkylated aromatic hydrocarbons. The aromatic hydrocarbon is preferably benzene. The polyalkylated aromatic hydrocarbon is preferably selected from diethylbenzene, and possibly triethylbenzene, and diisopropylbenzene, and possibly triisopropylbenzene. The transalkylation of benzene with diethylbenzene, and possibly triethylbenzene, to give ethylbenzene and benzene with diisopropylbenzene, and possibly triisopropylbenzene, to give cumene are particularly preferred.

The transalkylation reaction is preferably carried out under such conditions as to take place at least partially in liquid phase, more preferably under such conditions as to take place substantially in liquid phase. It is preferably carried out at a temperature of between 100 and 350° C., at a pressure of between 10 and 50 atms and at a WHSV of between 0.1 and 200 h$^{-1}$. The temperature is even more preferably between 150 and 300° C., the pressure between 20 and 45 atms and the WHSV between 0.1 and 10 h$^{-1}$.

The molar ratio between aromatic hydrocarbon and polyalkylaromatic hydrocarbon can vary between 1 and 30, preferably between 4 and 15.

According to a preferred aspect, in order to maximize the production of monoalkylated product in the reaction of aromatics with light olefins, and in particular benzene with ethylene to give ethylbenzene and benzene with propylene to give cumene, the transalkylation activity of the catalyst of the present invention can already be effected in the reactor in which the alkylation process is carried out, where by providing a sufficient residence time, the quantity of polyalkylated by-products is reduced with respect to the monoalkylated product. According to an even more preferred aspect, to obtain the best yields into monoalkylated product, the product obtained in alkylation can be separated into an aromatic hydrocarbon fraction, a monoalkylated aromatic fraction and a polyalkylated aromatic fraction and the latter fraction is refed to the alkylation reactor where it undergoes transalkylation to give the monoalkylated product.

Alternatively the transalkylation reaction can be carried out in a dedicated reactor, where the fraction of polyalkylaromatics is put in contact with a feeding of aromatic hydrocarbon, in the presence of the catalyst of the present invention. For example the "cumene bottoms" fraction produced in the alkylation process to give cumene can be used as polyalkylated aromatic hydrocarbon prevalently consisting of diisopropylbenzenes.

A further aspect of the present invention therefore relates to a process for preparing monoalkylated aromatic hydrocarbons which comprises:

1) putting an aromatic hydrocarbon and a $C_2$–$C_4$ olefin in contact with each other, in the presence of the catalyst of the present invention,
2) separating the product obtained into a fraction containing an aromatic hydrocarbon, a fraction containing a monoalkylated aromatic hydrocarbon and a fraction containing polyalkylated aromatic hydrocarbons,
3) putting the fraction containing the polyalkylated aromatic hydrocarbons in contact with an aromatic hydrocarbon, in the presence of the catalyst of the present invention.

According to the above, it is an even more prefered aspect of the present invention a process for preparing monoalkylated aromatic hydrocarbons which comprises:

1) putting an aromatic hydrocarbon and a $C_2$–$C_4$ olefin in contact with each other, in the presence of the catalyst of the present invention, under such alkylation conditions that the reaction takes place at least partially in liquid phase,
2) separating the product obtained into a fraction containing an aromatic hydrocarbon, a fraction containing a monoalkylated aromatic hydrocarbon and a fraction containing polyalkylated aromatic hydrocarbons,
3) putting the fraction containing the polyalkylated aromatic hydrocarbons in contact with an aromatic hydrocarbon, in the presence of the catalyst of the present invention, under such transalkylation conditions that the reaction takes place at least partially in liquid phase.

EXAMPLE 1

58.8 g of tetraethylammonium hydroxide at 40% by weight in aqueous solution and 1.9 g of sodium aluminate (56% of $Al_2O_3$) are added to 58.4 g of demineralized water. The mixture is heated to about 80° C. and is left under stirring until complete dissolution. The limpid solution thus obtained is added to 37.5 g of colloidal silica Ludox HS at 40% by weight of $SiO_2$. A homogeneous suspension is obtained, having a pH equal to 14, which is charged into a steel pressure-resistant reactor and left to crystallize under hydrothermal conditions at 150° C. for 10 days, under static conditions and at autogenous pressure. The crystallized product is separated by filtration, redispersed in demineralized water (about 150 g) and refiltered: a humid panel of zeolite is obtained containing the organic templating agent tetraethylammonium, and sodium. The product was characterized by X rays from powders.

EXAMPLE 2

The humid panel obtained in example 1 is dried in an oven for 1 hour at 150° C., and calcined in muffle for 5 hours at 550° C. in a stream of air.

The calcined solid is dispersed in an aqueous solution of ammonium acetate (150 g of water and 8 g of ammonium acetate) for the ion exchange. The suspension is heated under stirring for an hour at about 80° C.

The suspension is then filtered and the solid obtained is redispersed in demineralized water (150 ml) for the washing. The suspension is then refiltered and the ion exchange and washing are repeated in sequence. The solid is then washed again and refiltered and then dried in an oven for 1 hour at 150° C. thus obtaining the zeolite whose cationic sites are ammonium and alkylammonium ions. This zeolite is calcined in muffle for 5 hours at 550° C. in a stream of air thus obtaining the beta zeolite in acid form. Upon elemental analysis, the sodium residue in the latter sample is in fact equal to 106 ppm. The content of aluminum is equal to 3.14% [Al]/[Na]=252). The product was characterized by X-ray diffraction from powders.

EXAMPLE 3

The humid panel obtained in example 1 is redispersed in an aqueous solution of ammonium acetate (200 g of water and 16 g of ammonium acetate) for the ion exchange. This suspension is heated under stirring for an hour at about 80° C.

The suspension is then filtered and the solid obtained is redispersed in demineralized water (150 cc) for the washing. The suspension is then refiltered and a humid panel of beta zeolite is again obtained in whose cationic sites are ammonium and alkylammonium ions.

Upon elemental analysis, the sodium residue in the latter sample is in fact equal to 112 ppm. The content of aluminum is equal to 3.38% [Al]/[Na]=257).

The product was characterized by X-ray diffraction from powders.

EXAMPLE 4

A catalyst is prepared called CATALYST A1 based on beta zeolite prepared according to example 3 and alumina in the form of bohemite, according to an extrusion process whose main parameters adopted are indicated in table I.

The beta zeolite used for this preparation was not subjected to any calcination treatment. The preparation procedure is schematized in the flowsheet of FIG. 1. The catalyst thus obtained was then subjected to a single calcination treatment in air. Table I shows the ranges of porosity of the catalyst from which it can be observed that the fraction of pores with radius >100 Å is more than 35% in accordance with what is claimed in EP 687500, whereas the total volume of EPV extrazeolitic pores is equal to 0.81 ml/g.

Figure 2:
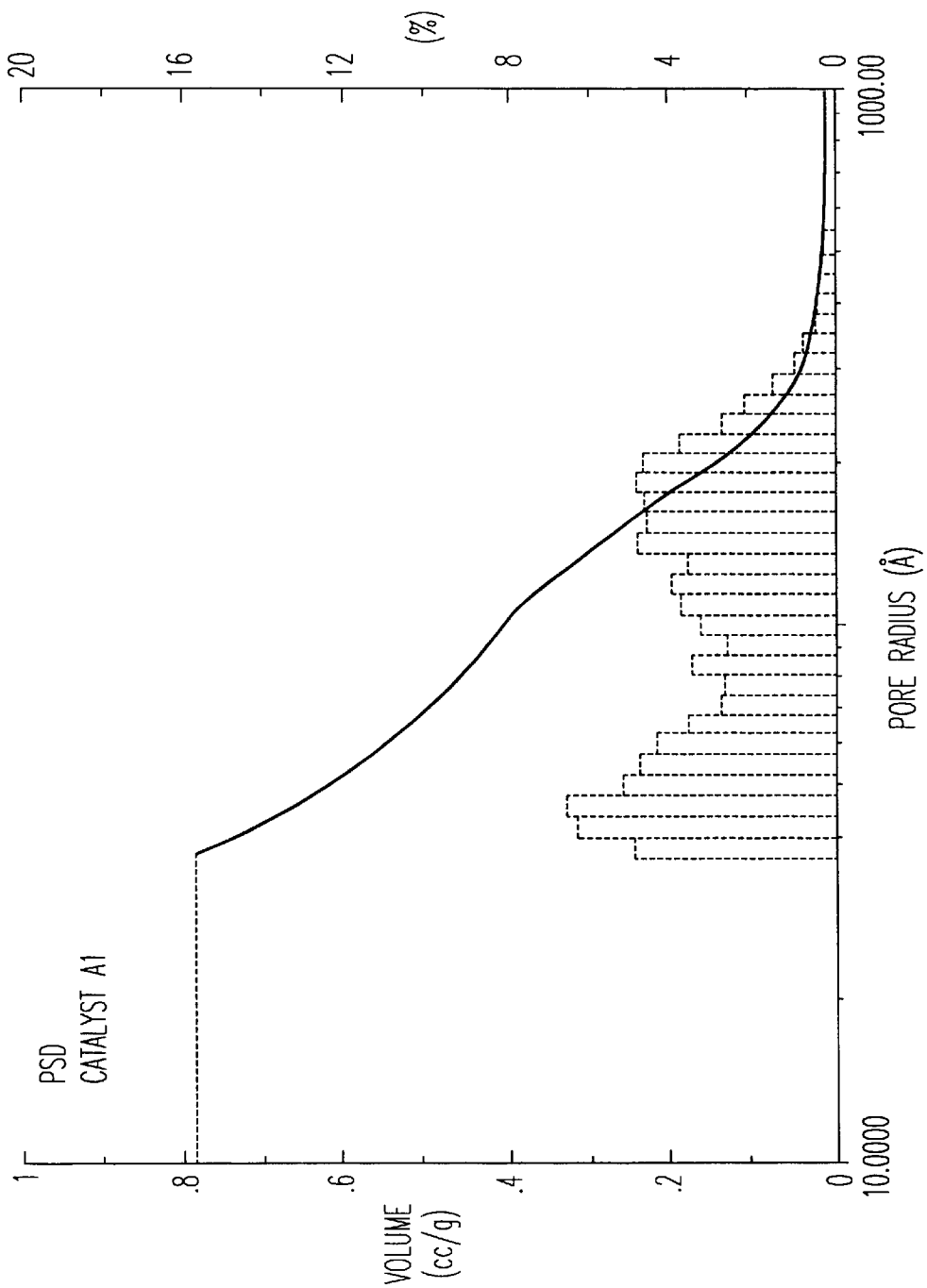
FIG. 2 is a graph of pore volume versus pore radius of catalyst A1.

FIG. 2 shows the graph of the extrazeolitic PSD relating to catalyst A1, to be compared with the volume of micropores, i.e. essentially zeolitic pores, equal to 0.12 ml/g.

Figure 3:
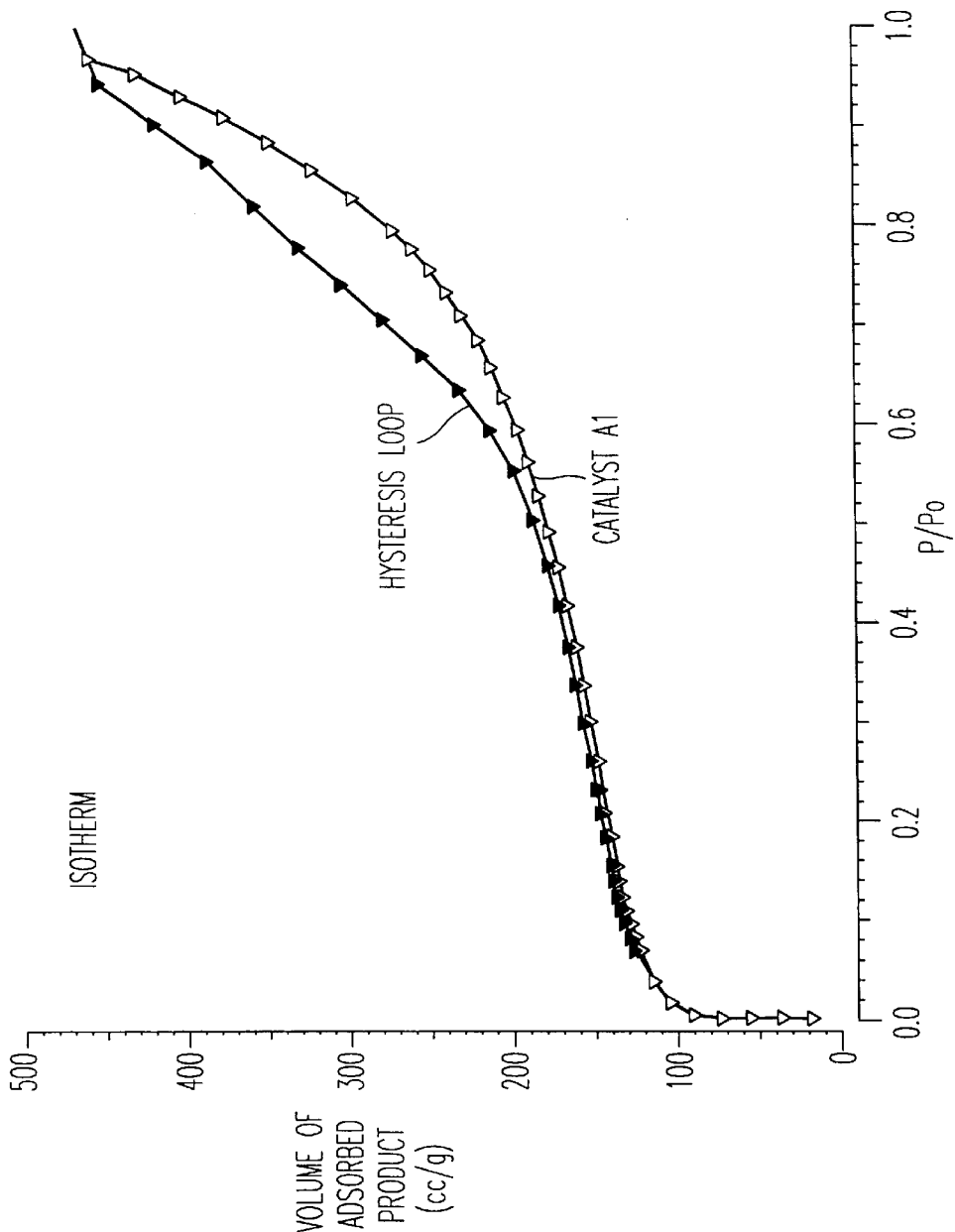
FIG. 3 is an absorption isotherm of nitrogen at liquid nitrogen temperature over catalyst A1.

FIG. 3 shows the complete absorption isotherm with nitrogen at the temperature of liquid nitrogen; the presence of hysteresis is due to the fraction of existing mesoporosity and its form gives a qualitative indication of the type of connectivity between the pores inside this fraction. The form of the hysteresis loop can be classified as type A.

The catalyst A1 has a Crushing Strength value equal to about 13 Kg/cm.

EXAMPLE 5 (comparative)

A catalyst is prepared called CATALYST A2 by means of an extrusion process whose main parameters are listed in table I starting from beta zeolite prepared according to example 3 and alumina in the form of bohemite.

The beta zeolite used for this preparation was not subjected to any calcination treatment. The main parameters of the extrusion process were modified with respect to those used in the previous example 4. The preparation procedure is schematized in the flowsheet of FIG. 1. The catalyst thus obtained was then subjected to a single calcination treatment in air.

Figure 4:
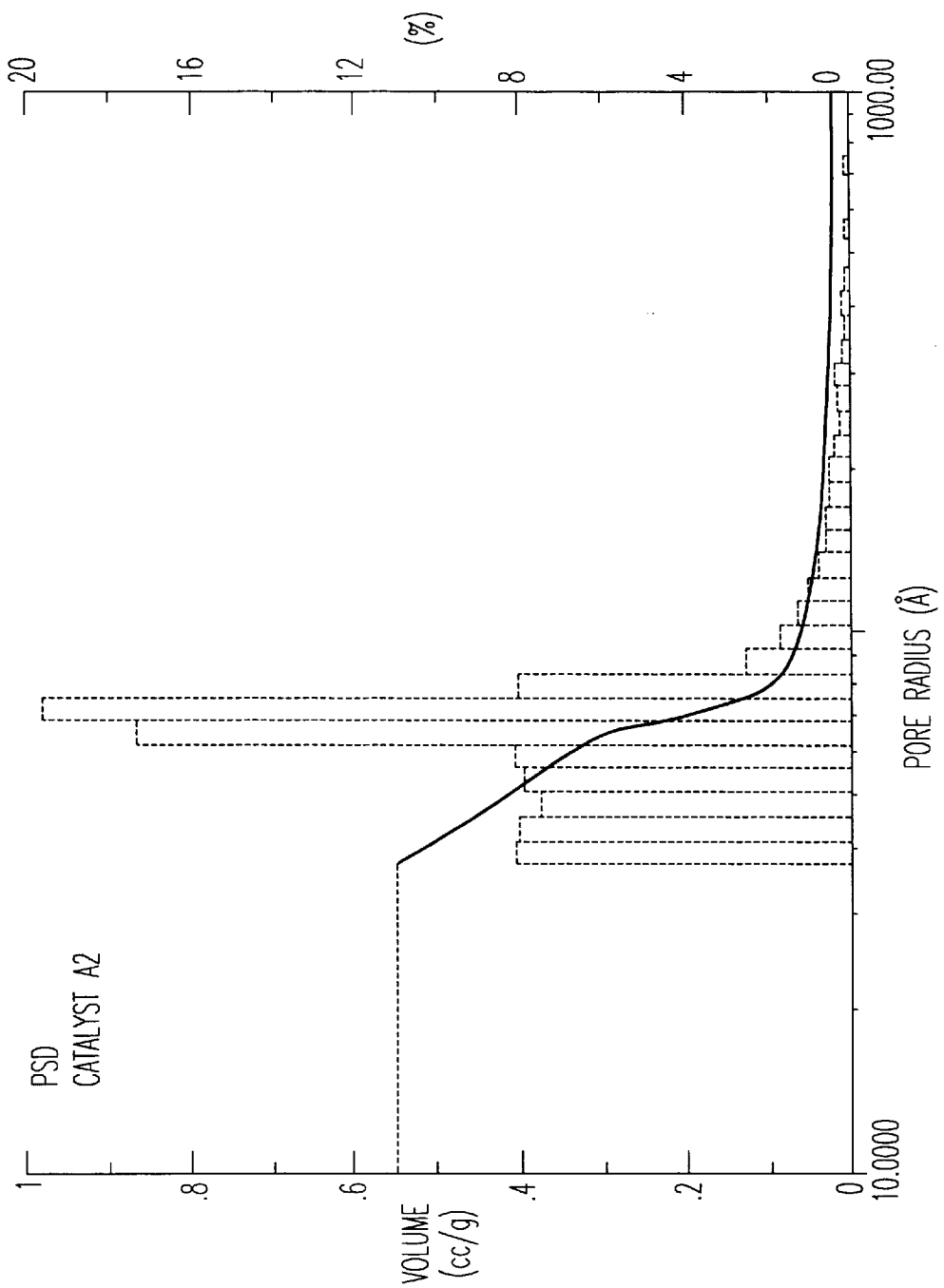
FIG. 4 is a graph of pore volume versus pore radius of catalyst A2.

Table I shows the ranges of porosity of the catalyst from which it can be observed that the fraction of pores with radius >100 Å is less than 25% of the total extrazeolite porosity unlike what is claimed in EP 687500, whereas the total volume of EPV extrazeolitic pores is equal to 0.55 cc/g:

FIG. 4 shows the graph of the extrazeolitic PSD relating to catalyst A2, which clearly shows the absence of the characteristics of extrazeolite porosity of the material A1.

The catalyst A2 has a Crushing Strength equal to about 15.1 Kg/cm.

EXAMPLE 6 (comparative)

A catalyst is prepared called CATALYST A3 by means of an extrusion process whose main parameters are listed in table I starting from beta zeolite prepared according to example 2 and alumina in the form of bohemite.

The beta zeolite used for this preparation was subjected to preventive calcination treatment. The main parameters of the extrusion process were modified with respect to those used in the previous example 4. The preparation procedure is schematized in the flowsheet of FIG. 1. Table I shows the ranges of porosity of the catalyst from which it can be observed that the fraction of pores with radius >100 Å is less than 25% of the total extrazeolite porosity unlike what is claimed in EP 687500, whereas the total volume of EPV extrazeolitic pores is equal to 0.21 cc/g.

Figure 5:
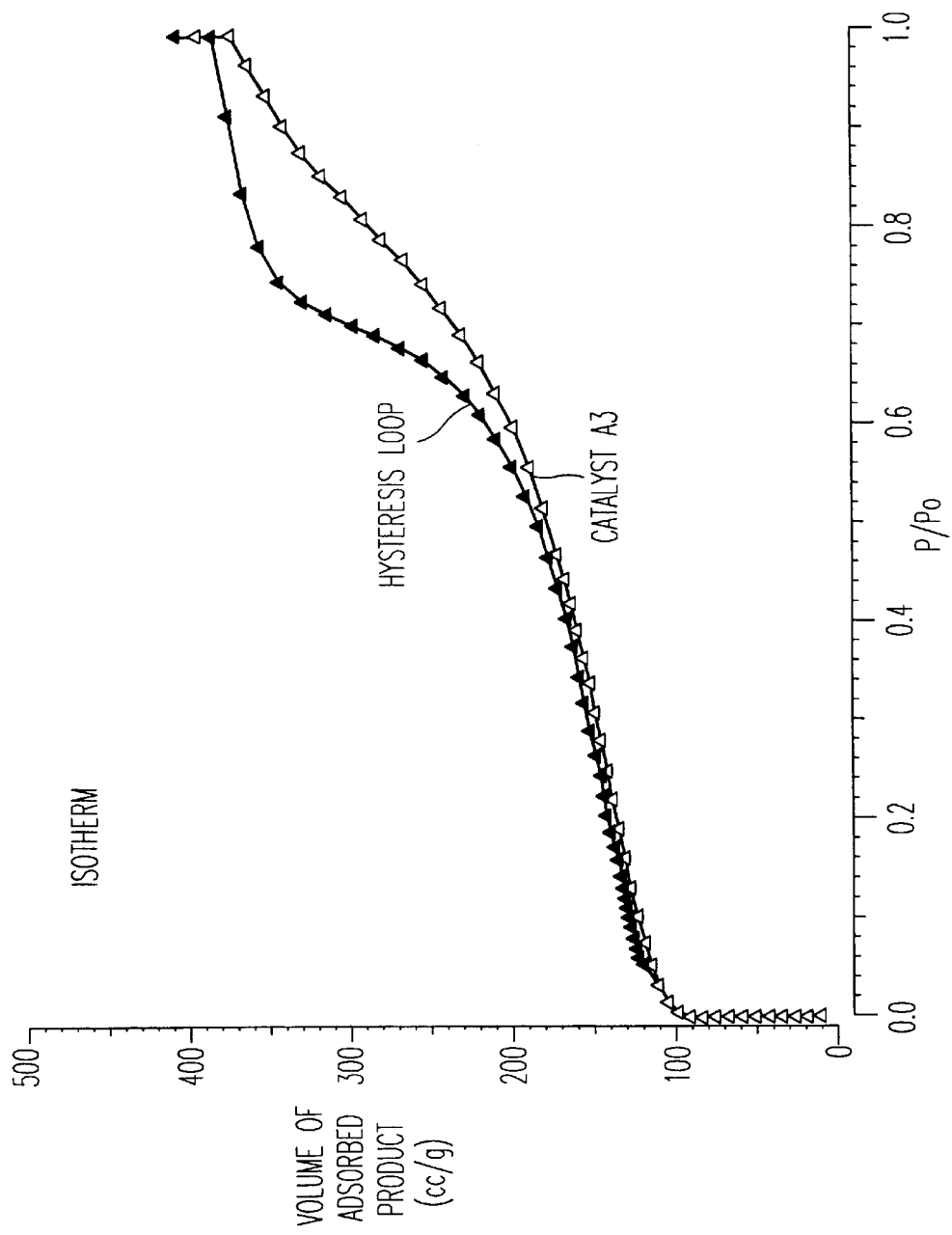
FIG. 5 is the absorption isotherm of nitrogen at liquid nitrogen temperature over catalyst A3.

FIG. 5 shows the complete absorption isotherm with nitrogen at the temperature of liquid nitrogen; the presence of hysteresis is due to the fraction of existing mesoporosity and its form gives a qualitative indication of the type of connectivity between the pores inside this fraction. The form of the hysteresis loop can be classified as type E. In fact, as can be seen, the hysteresis is much more marked than that of FIG. 3 in the sense that in the first section, with the lowering of the relative pressure along the desorption branch there is a smaller quantity of vapour with respect to what is indicated in FIG. 3. This is due to the greater difficulty of the adsorbed product to be desorbed by the pores in which it is contained, evidently owing to the lesser connectivity which characterizes the porous network of the material A3 with respect to the material A1.

EXAMPLE 7 (catalytic test)

An alkylation test of benzene with propylene is carried out using an experimental device consisting of a micropilot reactor with a catalyst fixed bed made of Inconel 600 with an internal diameter of 2 cm and total length of 80 cm, feeding tanks of the benzene and propylene, dosage pumps for the separate feeding of the two reagents in liquid phase, temperature and pressure control, automatic discharge of the reactor effluent and automatic sampling system of the feeding and effluent from the reactor for the continual analysis of the reagents and products.

This analysis is carried out by an HP 5890 gas-chromatograph connected to a processor, He transport gas, $\frac{1}{8}"\times 1.5$ mt steel column packed with FFAP 15% on Chromosorb W-AW, injector temperature 250° C., Temperature program from 50 to 220° C., temperature of the detector 250° C. and TCD detector for the feeding to the reactor.

The effluent from the reactor on the other hand is analyzed with a DANI 8520 gas-chromatograph connected to a processor, He transport gas, capillary column of molten silica with an internal diameter of 0.2 mm, a length of 50 mt and methylsilicon distribution liquid 0.5 microns, injector temperature 250° C., temperature a program from 40 to 240° C., temperature of the detector 250° C. and FID detector.

The reaction conditions adopted during the test are the following:

T inlet=150° C.
P=30 bars
WHSV=5.5 hr$^{-1}$
[Benzene[/[Propylene]=5.7

4.5 g of catalyst prepared as described in example 4 (CATALYST A1) and 11.5 g of inert material are then charged.

Figure 6:
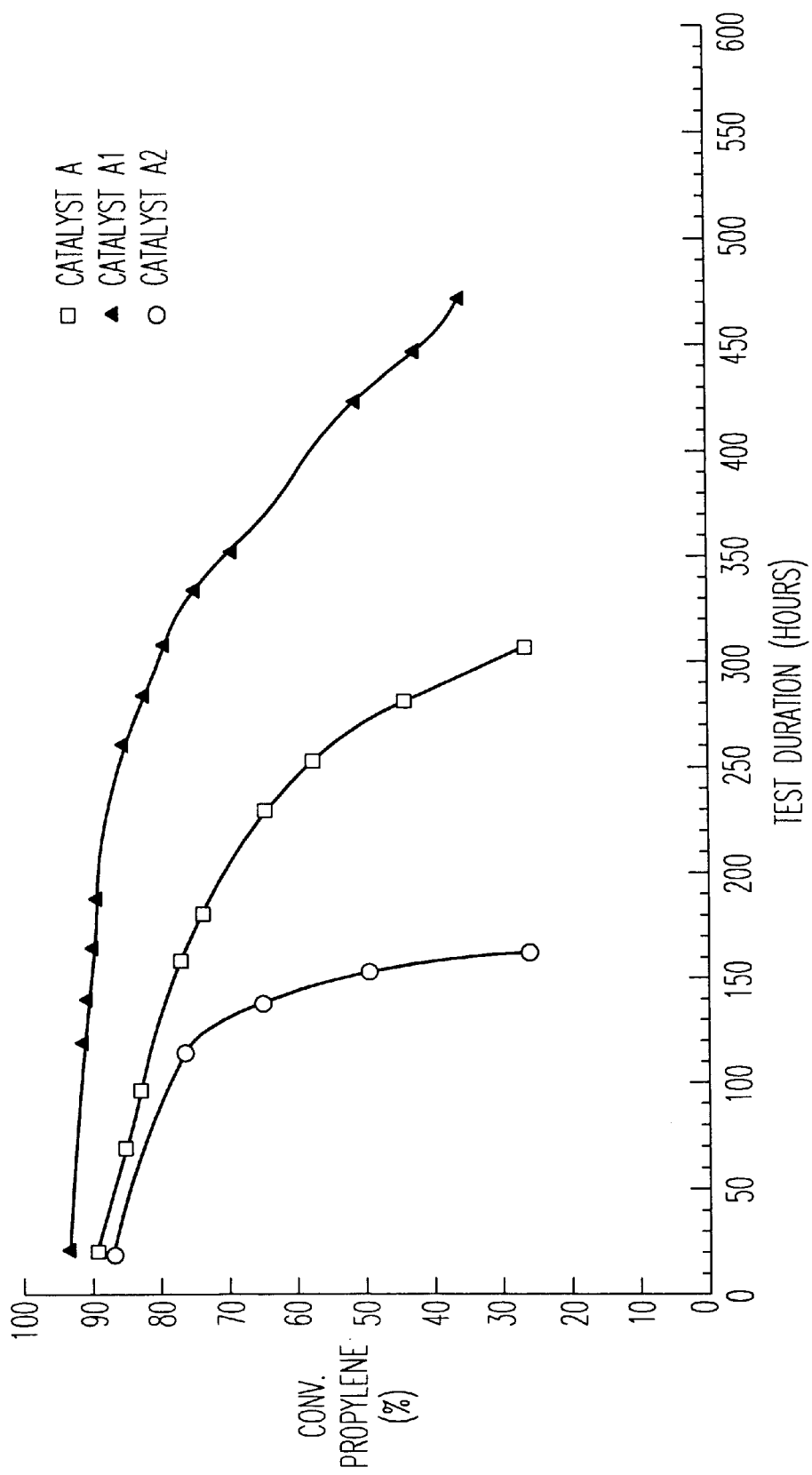
FIG. 6 is a graph of propylene conversion versus time on catalyst A1.

FIG. 6 shows the trend of the propylene conversion in ordinate (%) in relation to the "time on stream" in hours in abscissa obtained using a bench reactor.

As can be seen from FIG. 6, the conversion of the propylene at the end of the test was equal to about 35% after 500 hours of continuous running without any modification of the above reaction conditions.

The same FIG. 6 indicates for comparative purposes the curve relating to the test carried out on catalyst A prepared according to what is described in example 1 of EP 687500.

As can be seen the improvement in terms of productivity is considerable and can be attributed to the combination of a particular PSD with a high total extrazeolitic pore volume.

EXAMPLE 8 (Comparative)

Under the same conditions and in the same experimental device as example 7, a catalytic test is carried out charging catalyst A2 prepared according to what is described in example 5. FIG. 6 shows the trend of the propylene conversion in relation to the time on stream. As can be seen, after about 160 hours of running the propylene conversion went down to about 26%.

EXAMPLE 9 (catalytic test)

An alkylation test of benzene with ethylene is carried out on a micropilot plant consisting of two fixed-bed reactors situated in series, with split feeding of the ethylene. These tubular reactors are made of AISI 316 steel with an internal diameter equal to 1.4 cm and a length equal to 25.1 cm.

Each reactor is equipped with eight thermocouples arranged along the catalytic bed and operates adiabatically. The benzene is fed by means of a dosage pump, through a preheater, into the lower part of the first reactor. The ethylene is measured by means of a mass measurer and mixed with the benzene before being introduced into the preheaters. The reaction mixture, at the outlet of the second reactor passes through a pressure-regulation system and is finally cooled and collected in a tank. In each tank, the molar ratio benzene/ethylene is equal to 10 and therefore the overall molar ratio is equal to 5. The inlet temperature in each reactor is equal to 200° C. and the pressure is maintained at 40 bars. The position of the temperature peak is determined by the thermal profile graph revealed by the thermocouples. The alkylated liquid produced is analyzed by gaschromatography. The reactors are charged with the catalyst A1 prepared according to what is described in example 4. Assuming that after N hours of running the catalyst included between the beginning of the bed and a thermocouple used as reference, is deactivated, the productivity of the catalyst is defined as grams of ethylbenzene produced per grams of deactivated catalyst.

Figure 7:
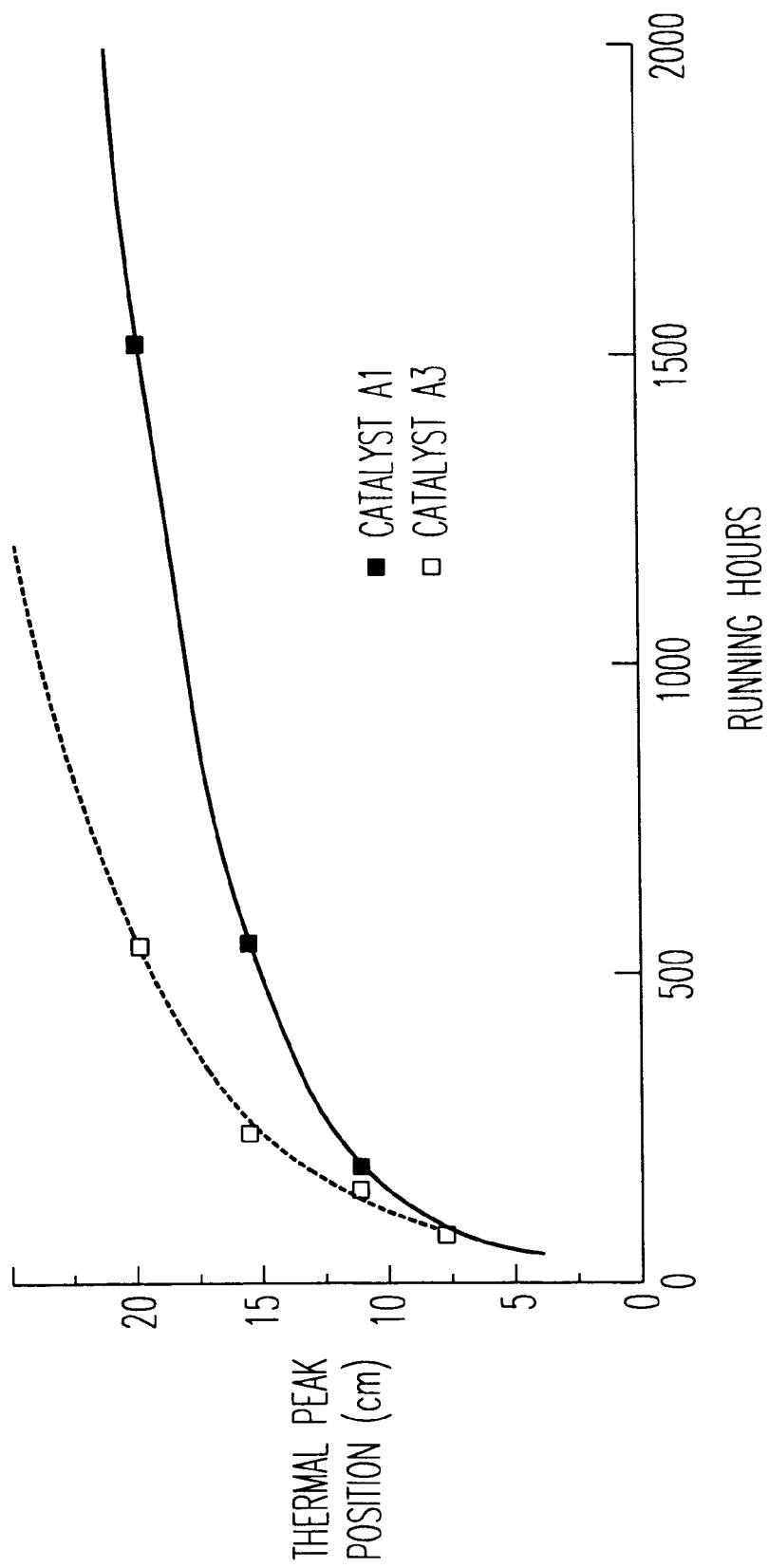
FIG. 7 is a graph of the trend of the thermal peak along a reactor versus time on stream of Example 9.

FIG. 7 shows the trend of the thermal peak along the reactor revealed in the points indicated by means of the corresponding thermocouples, in relation to the time on stream. If the seventh thermocouple situated inside the first reactor at approximately 20 cm from the beginning of the catalytic bed, is taken as reference, the productivity of the catalyst proves to be equal to 2050 Kg of ethylbenzene per Kg of catalyst after 1500 hours of running.

EXAMPLE 10 (comparative catalytic test)

A test is carried out under the same conditions and in the same experimental device described in example 9 but using the catalyst A3 prepared according to what is described in example 6.

FIG. 7 shows the trend of the thermal peak along the reactor revealed in the points indicated by means of the corresponding thermocouples, in relation to the time on stream.

Calculating the productivity of the catalyst as in example 9, there is a value equal to 750 Kg of ethylbenzene per Kg of catalyst after 550 hours of running.

EXAMPLE 11 (catalytic test)

6 g of extruded catalyst A1 prepared according to example 4 are charged into a fixed-bed reactor. The reagents (benzene and propylene in a molar ratio 7/1) are fed separately to the reactor where the alkylation reaction to cumene takes place at a temperature of 150° C. and 38 bars of pressure. The flow-rates of the feeding are such as to obtain WHSV values=0.71, 0.43, 0.14 $h^{-1}$. The results are shown in the following table (the conversion of the cumene is total in all three cases):

| WHSV ($h^{-1}$) | DIPB (Kg/ton cumene) |
|---|---|
| 0.71 | 74.32 |
| 0.43 | 63.82 |
| 0.14 | 55.7 |

The decrease in the selectivity of the diisopropylbenzenes with a decrease in the WHSV is due to the their transalkylation in the presence of benzene.

EXAMPLE 12 (comparative catalytic test)

The reaction of the previous example 11 is repeated using as catalyst, catalyst A prepared according to example 1 of EP 687500. The results are shown in the following table (also in this case the conversion of the propylene is total):

| WHSV ($h^{-1}$) | DIPB (Kg/ton cumene) |
|---|---|
| 0.71 | 85.41 |
| 0.43 | 74.23 |
| 0.14 | 66.47 |

From a comparison with the results obtained in example 11, it is evident that the catalyst of the present invention is more selective than the catalyst of EP 687500, as with the same conversion of the propylene (total with both catalysts) it forms less diisopropylbenzene.

EXAMPLE 13 (transalkylation catalytic test)

A transalkylation test with benzene is carried out using a mixture whose composition is indicated in the following table, which simulates a typical composition of cumene bottoms. The reaction conditions are also indicated in the following table:

| Cumene bottoms | % (w/w) | reaction conditions |
|---|---|---|
| cumene | 5.2 | temp. = 200° C. |
| n-propylbenzene | 130 ppm | press. = 30 bars |
| phenyl—$C_4$ | 0.5 | benzene = 250 g |
| phenyl—$C_5$ | 0.8 | cumene bottoms = 90 g |
| m,o,p diisopropyl- | 73.6 | catalyst = 3.5 g |
| heavy products | 19.8 | |

Figure 8:
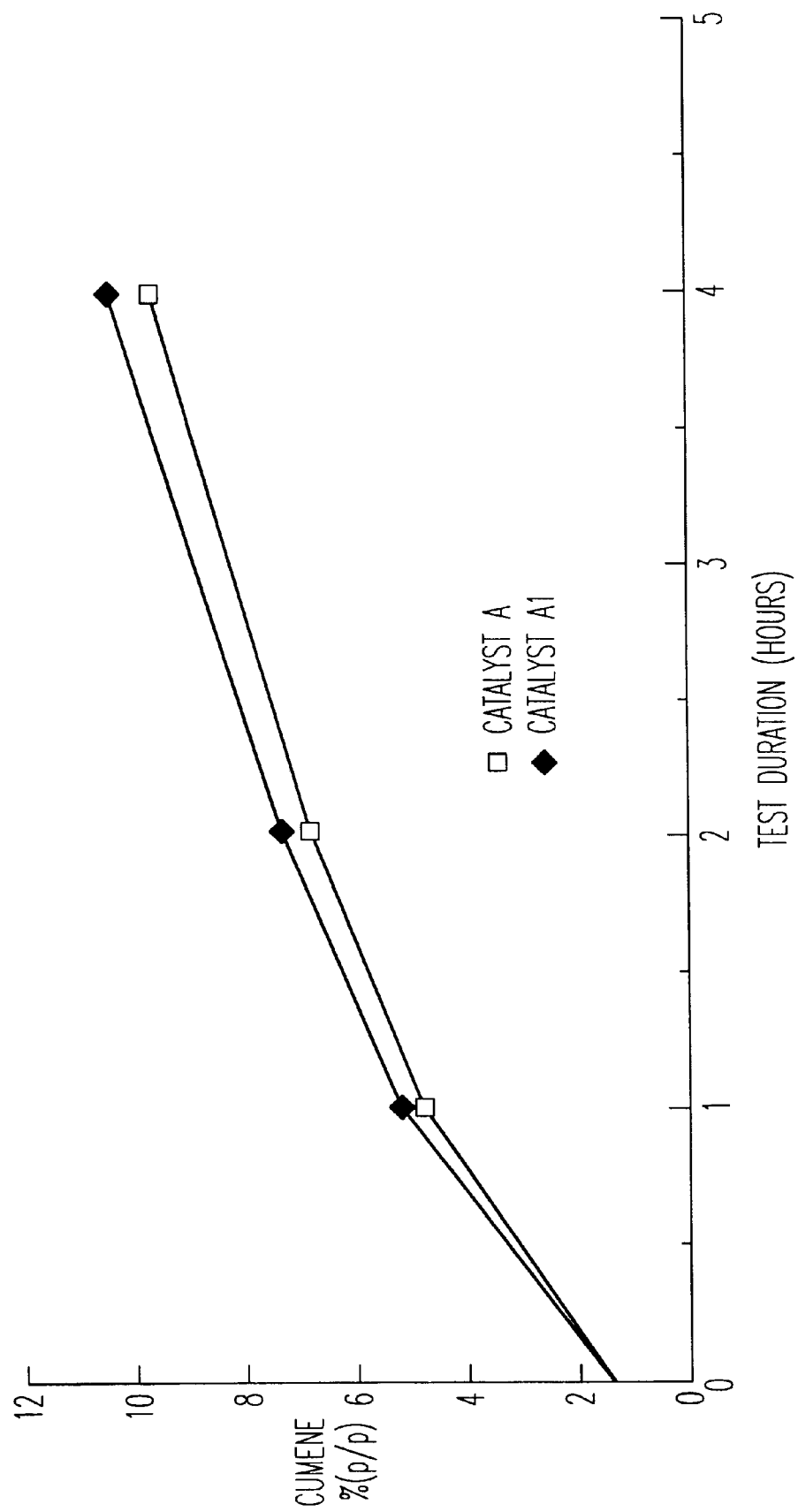
FIG. 8 is a graph of cumene production versus time in the transalkylation of benzene with cumene bottoms.

The catalysts used in this test are catalyst A1 prepared according to example 3 and comparative catalyst A prepared according to example 1 of patent application EP 687500. The results, expressed as % (w/w) of cumene in the reaction mixture in ordinate in relation to the duration of the test in hours in abscissa, are indicated in the graph of FIG. 8.

TABLE 1

|  | Catalyst A1 | Catalyst A2 | Catalyst A3 | Catalyst A(***) |
|---|---|---|---|---|
| Catalyst preparation data | | | | |
| Ligand content (w/w %) | 50 | 50 | 50 | 50 |
| Peptizing agent | Acetic acid | Acetic acid | Acetic acid | Acetic acid |
| Peptizing agent/ligand (w/w) | 0.028 | 0.058 | 0.121 | 0.034 |
| Mixing time before extrusion(*) | 45 | 55 | 55 | 55 |
| Calcination temperature (° C.) | 550 | 550 | 550 | 550 |
| Catalyst data | | | | |
| Spec. surf area ($N_2$ ads. BET 3 param.) | 482 | 463 | 468 | 460 |
| Extrazeolite Pore Volume EPV (cc/g)(**) | 0.81 | 0.58 | 0.23 | 0.40 |
| EPV fraction with 15 A < pare radius < 100 A | 0.41 | 0.52 | 0.16 | 0.14 |
| EPV fraction with 100 A < pare radius < 1000 A | 0.39 | 0.04 | 0.07 | 0.25 |
| EPV fraction with 1000 A < pare radius < 75000 A | 0.01 | 0.02 | 0 | 0.01 |
| Crushing strength along the diameter (Kg/cm) | 13 | 15.1 | 19 | 7 |

(*)Dry powders mixing time + damp powders mixing time
(**)15 A < Pore radius < 75000 A
(***)From EP 0 678 500 A1, Ex. 1 page 6 and table I page 10

We claim:

1. A catalyst for the alkylation and/or transalkylation of aromatic compounds, consisting of:
   i) beta zeolite or beta zeolite modified by the isomorphous substitution of aluminum with boron, iron or gallium or modified by the introduction of alkali and/or alkaline earth metals therein by means of ion exchange; and
   ii) an inorganic binder, wherein at least 25% of the pore volume obtained by adding the fractions of mesoporosity and macroporosity present in the catalyst itself consists of pores having a radius greater than 100 Å, said catalyst having a pore volume, obtained by adding the fractions of mesoporosity and macroporosity, of $\geq 0.80$ ml/g.

2. The catalyst according to claim 1, wherein the beta zeolite is in the form in which most of the cationic sites are occupied by hydrogen ions.

3. The catalyst according to claim 1, wherein the inorganic binder is selected from the group consisting of oxides of silicon, aluminum or magnesium, or natural clays and combinations thereof.

4. The catalyst according to claim 1, wherein said pore volume is at least 35%.

5. A process for the preparation of the catalyst of claim 1, which comprises:
   a) preparing a homogenous mixture comprising beta zeolite whose cationic sites are ammonium and alkylammonium ions and an inorganic ligand;
   b) shaping the mixture thus obtained into an object; and
   c) calcining the object prepared in step (b).

6. The process according to claim 5, wherein, in step (a), the beta zeolite, whose cationic sites are ammonium and alkylammonium ions, is mixed with said ligand in relative quantities ranging from 50:50 to 95:5.

7. The process according to claim 6, wherein said quantitative range is 70:30 to 90:10.

8. The process according to claim 5, wherein the binder is selected from the group consisting of oxides of aluminum, silicon or magnesium, natural clays and combinations thereof.

9. The process according to claim 5, wherein the mixture prepared in step (a) contains a material selected from the group consisting of a peptizing agent, a plasticizer and mixtures thereof.

10. The process according to claim 5, wherein the calcination of step (c) is carried out in air at a temperature ranging from 400 to 600° C.

11. The process according to claim 5, wherein the calcination step is preceded by an aging and drying step at a temperature ranging from room temperature to 200° C.

12. A process for the alkylation of aromatic hydrocarbons, comprising:
    alkylating said aromatic hydrocarbon with a $C_2$–$C_4$-olefin in the presence of the catalyst of claim 1.

13. The process according to claim 12, wherein the alkylation reaction takes place under at least partial liquid phase condition.

14. The process according to claim 12 which occurs at a temperature ranging from 100 to 300° C., at a pressure ranging from 10 to 50 atms, at a WHSV space velocity ranging from 0.1 to 200 $h^{-1}$ and with a molar ratio ranging from 1 to 20.

15. The process according to claim 14, wherein the temperature ranges from 120 to 230° C., the pressure from 20 to 45 atms and the WHSV space velocity from 1 to 10 $h^{-1}$.

16. The process according to claim 14, wherein the molar ratio of aromatic hydrocarbon to olefin ranges from 2 to 8.

17. The process according to claim 12, wherein the aromatic hydrocarbon is benzene.

18. The process according to claim 12, wherein the olefin is ethylene or propylene.

19. The process according to claim 12, wherein the aromatic hydrocarbon is benzene and the olefin is ethylene.

20. The process according to claim 12, wherein the aromatic hydrocarbon is benzene and the olefin is propylene.

21. The process according to claim 12, wherein the olefin, aromatic hydrocarbon or a combination thereof is added to the reaction in more than one step.

22. A process for the transalkylation of aromatic hydrocarbons, which comprises:
    transalkylating an aromatic hydrocarbon with a polyalkylated aromatic hydrocarbon in the presence of the catalyst of claim 1.

23. The process according to claim 22 wherein the transalkylation reaction occurs at least partially in the liquid phase.

24. The process according to claim 22, which occurs at a temperature ranging from 100 to 350° C., at a pressure ranging from 10 to 50 atms, at a WHSV space velocity ranging from 0.1 to 200 $h^{-1}$.

25. The process according to claim 24, wherein the temperature ranges from 150 to 300° C., the pressure from 20 to 45 atms and the WHSV space velocity from 0.1 to 10 $h^{-1}$.

26. The process according to claim 24, wherein the molar ratio of the aromatic hydrocarbon and polyalkylaromatic hydrocarbon ranges from 1 and 30.

27. The process according to claim 22, wherein the aromatic hydrocarbon is benzene.

28. The process according to claim 22, wherein the polyalkylated aromatic hydrocarbon is diethylbenzene or diisopropylbenzene.

29. A process for preparing monoalkylated aromatic hydrocarbons, which comprises:
   i) alkylating an aromatic hydrocarbon with a $C_2$–$C_4$ olefin in the presence of the catalyst of claim 11;
   ii) separating the product obtained into an aromatic hydrocarbon fraction, a monoalkylated aromatic hydrocarbon fraction and a polyalkylated aromatic hydrocarbon fraction; and
   iii) reacting the polyalkylated aromatic hydrocarbon fraction with an aromatic hydrocarbon in the presence of the catalyst of claim 1, thereby preparing monoalkylated aromatic hydrocarbon product.

30. The process according to claim 29, wherein the alkylating step i) occurs at least partially in the liquid phase, and wherein the transalkylating reaction conditions of step iii) occur under at least partial liquid phase conditions.

* * * * *